(12) United States Patent
Noddin

(10) Patent No.: US 8,876,763 B2
(45) Date of Patent: Nov. 4, 2014

(54) COMPOSITE BALLOON

(75) Inventor: Richard Noddin, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2720 days.

(21) Appl. No.: 11/265,388

(22) Filed: Nov. 1, 2005

(65) Prior Publication Data
US 2007/0106216 A1 May 10, 2007

(51) Int. Cl.
*A61M 31/00* (2006.01)
*A61M 37/00* (2006.01)
*A61M 25/10* (2013.01)

(52) U.S. Cl.
CPC ... *A61M 25/1029* (2013.01); *A61M 2025/1084* (2013.01); *A61M 2025/1075* (2013.01)
USPC .................. 604/103.09; 604/103.06

(58) Field of Classification Search
CPC ................ A61M 25/1029; A61M 2025/1029; A61M 2025/1084
USPC .................. 604/101.02, 103, 103.01, 103.02, 604/103.05, 103.06, 103.08, 103.09, 604/103.11–103.14
See application file for complete search history.

(56) References Cited

U.S. PATENT DOCUMENTS

| | | | |
|---|---|---|---|
| 4,490,421 A | 12/1984 | Levy | 428/36.9 |
| 4,637,396 A | 1/1987 | Cook | 128/344 |
| 4,906,244 A | 3/1990 | Pinchuk et al. | 606/194 |
| 4,950,239 A | 8/1990 | Gahara et al. | 604/96.01 |
| 5,201,706 A | 4/1993 | Noguchi et al. | 604/96 |
| 5,250,069 A | 10/1993 | Nobuyoshi et al. | 606/192 |
| 5,264,260 A | 11/1993 | Saab | 428/35.5 |
| 5,270,086 A | 12/1993 | Hamlin | 428/35.2 |
| 5,328,468 A | 7/1994 | Kaneko | 604/103.13 |
| 5,344,400 A | 9/1994 | Kaneko | 604/103.06 |
| 5,344,401 A | 9/1994 | Radisch et al. | 604/96 |
| 5,500,180 A | 3/1996 | Anderson et al. | 264/532 |
| 5,510,077 A | 4/1996 | Dinh et al. | 264/485 |
| 5,522,818 A | 6/1996 | Keith et al. | 604/102 |
| 5,533,516 A * | 7/1996 | Sahatjian | 600/562 |
| 5,554,182 A | 9/1996 | Dinh et al. | 623/1 |
| 5,556,383 A | 9/1996 | Wang et al. | 604/103.11 |
| 5,571,166 A | 11/1996 | Dinh et al. | 623/1 |
| 5,587,125 A | 12/1996 | Roychowdhury | 264/515 |
| 5,591,224 A | 1/1997 | Schwartz et al. | 623/1 |
| 5,591,227 A | 1/1997 | Dinh et al. | 623/1 |
| 5,599,352 A | 2/1997 | Dinh et al. | 623/1 |

(Continued)

FOREIGN PATENT DOCUMENTS

| | | |
|---|---|---|
| EP | 0 783 897 A2 | 7/1997 |
| EP | 0 783 897 A3 | 8/1999 |
| WO | 01/49337 | 7/2001 |
| WO | 2004/004820 | 1/2004 |

OTHER PUBLICATIONS

U.S. Appl. No. 10/849,742, filed May 20, 2004, Chen, Weber.
U.S. Appl. No. 11/085,780, filed Mar. 21, 2005, Weber et al.

(Continued)

*Primary Examiner* — Nathan R Price
(74) *Attorney, Agent, or Firm* — Vidas, Arrett & Steinkraus

(57) ABSTRACT

A reinforced composite balloon may comprise a body layer and a reinforcing layer. The reinforcing layer may comprise a single-layer structural network having a plurality of apertures. The reinforcing layer may be molded from a reinforcing tube having a plurality of apertures or aperture precursor holes.

17 Claims, 13 Drawing Sheets

(56) References Cited

U.S. PATENT DOCUMENTS

| | | | |
|---|---|---|---|
| 5,628,785 A | 5/1997 | Schwartz et al. | 623/1 |
| 5,693,014 A * | 12/1997 | Abele et al. | 604/103.08 |
| 5,697,967 A | 12/1997 | Dinh et al. | 623/1 |
| 5,702,439 A | 12/1997 | Keith et al. | 604/96 |
| 5,792,415 A | 8/1998 | Hijlkema | 264/530 |
| 5,797,877 A | 8/1998 | Hamilton et al. | 604/96.01 |
| 5,833,657 A | 11/1998 | Reinhardt et al. | 604/53 |
| 5,855,563 A | 1/1999 | Kaplan et al. | 604/49 |
| 5,944,726 A | 8/1999 | Blaeser et al. | 606/108 |
| 5,948,345 A | 9/1999 | Patel et al. | 264/529 |
| 5,984,345 A | 11/1999 | Carter | 280/633 |
| 6,004,289 A | 12/1999 | Saab | 604/96 |
| 6,048,332 A * | 4/2000 | Duffy et al. | 604/103.08 |
| 6,086,556 A | 7/2000 | Hamilton et al. | 604/96 |
| 6,124,007 A | 9/2000 | Wang et al. | 428/35.2 |
| 6,146,356 A | 11/2000 | Wang et al. | 604/96.01 |
| 6,156,254 A | 12/2000 | Andrews et al. | 264/231 |
| 6,206,914 B1 | 3/2001 | Soykan et al. | 623/1.42 |
| 6,228,845 B1 | 5/2001 | Donovan et al. | 514/44 |
| 6,258,099 B1 | 7/2001 | Mareiro et al. | 606/108 |
| 6,270,522 B1 | 8/2001 | Simhambhatla et al. | 623/1.11 |
| 6,273,879 B1 | 8/2001 | Keith et al. | 604/523 |
| 6,280,411 B1 * | 8/2001 | Lennox | 604/103.05 |
| 6,328,710 B1 | 12/2001 | Wang et al. | 604/96.01 |
| 6,364,856 B1 | 4/2002 | Ding et al. | |
| 6,391,032 B2 | 5/2002 | Blaeser et al. | 606/108 |
| 6,544,223 B1 | 4/2003 | Kokish | 604/103.01 |
| 6,652,485 B1 | 11/2003 | Gaudoin et al. | 604/103.07 |
| 6,676,667 B2 | 1/2004 | Mareiro et al. | 606/108 |
| 6,695,809 B1 | 2/2004 | Lee | 604/96.01 |
| 6,733,487 B2 | 5/2004 | Keith et al. | 604/526 |
| 6,736,841 B2 | 5/2004 | Musbach et al. | 623/1.11 |
| 6,746,425 B1 | 6/2004 | Beckham | 604/103.09 |
| 6,786,889 B1 | 9/2004 | Musbach et al. | 604/103.08 |
| 6,802,849 B2 | 10/2004 | Blaeser et al. | 606/191 |
| 6,951,675 B2 | 10/2005 | Chin et al. | 428/35.7 |
| 6,977,103 B2 | 12/2005 | Chen et al. | 428/35.7 |
| 7,309,324 B2 * | 12/2007 | Hayes et al. | 604/96.01 |
| 7,632,242 B2 * | 12/2009 | Griffin et al. | 604/96.01 |
| 2002/0151844 A1 | 10/2002 | Yang et al. | 604/103.02 |
| 2004/0181252 A1 | 9/2004 | Boyle et al. | 606/194 |
| 2004/0207127 A1 | 10/2004 | Hamlin | 264/540 |
| 2005/0182361 A1 | 8/2005 | Lennox | 604/103.01 |
| 2005/0261760 A1 | 11/2005 | Weber | 623/1.38 |
| 2005/0271844 A1 | 12/2005 | Mapes et al. | 428/36.1 |

OTHER PUBLICATIONS

U.S. Appl. No. 10/849,742, filed May 20, 2004, John Chen.
U.S. Appl. No. 11/085,780, filed Mar. 21, 2005, Jan Weber, Karl Jagger, Liliana Atanasoska.

* cited by examiner

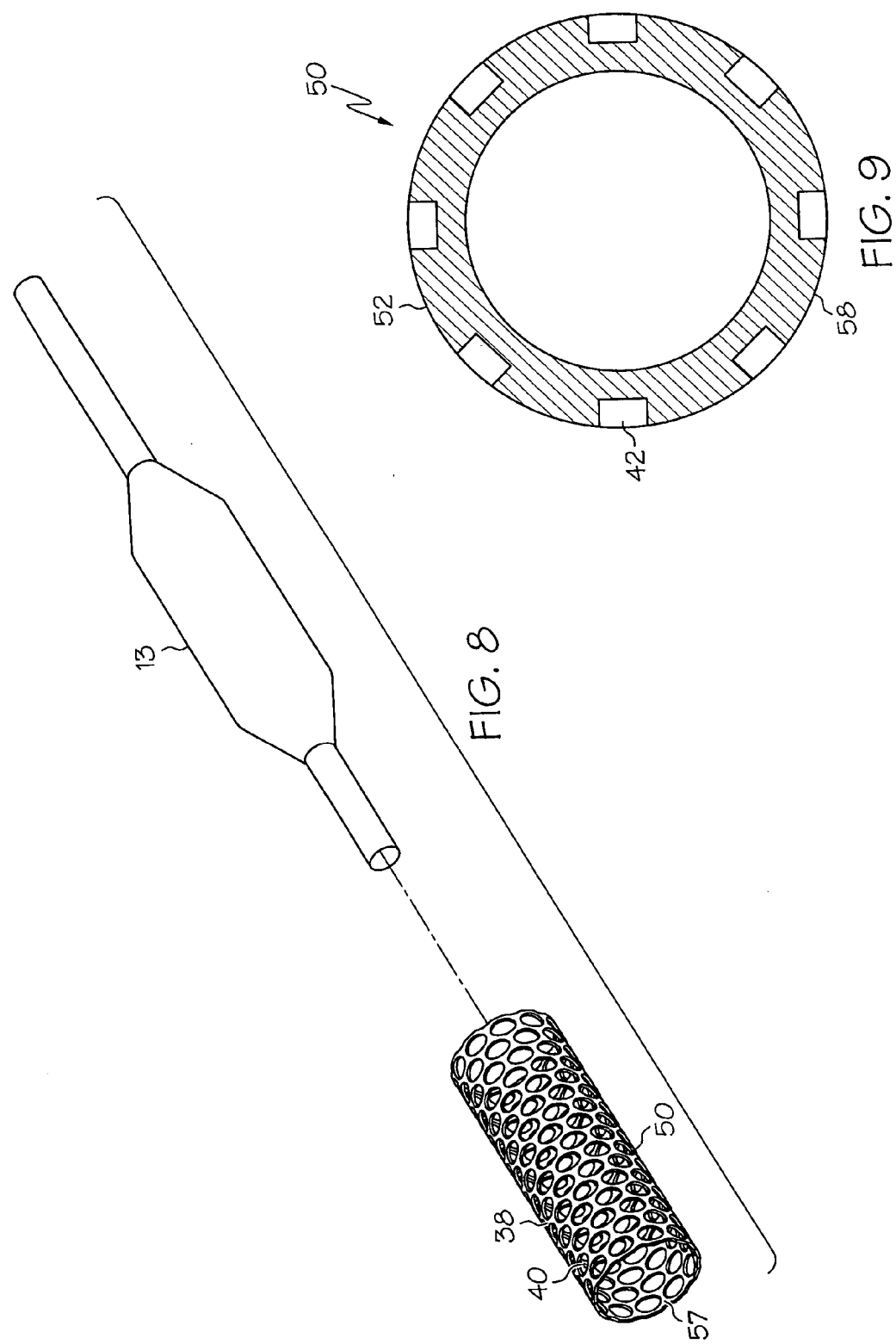

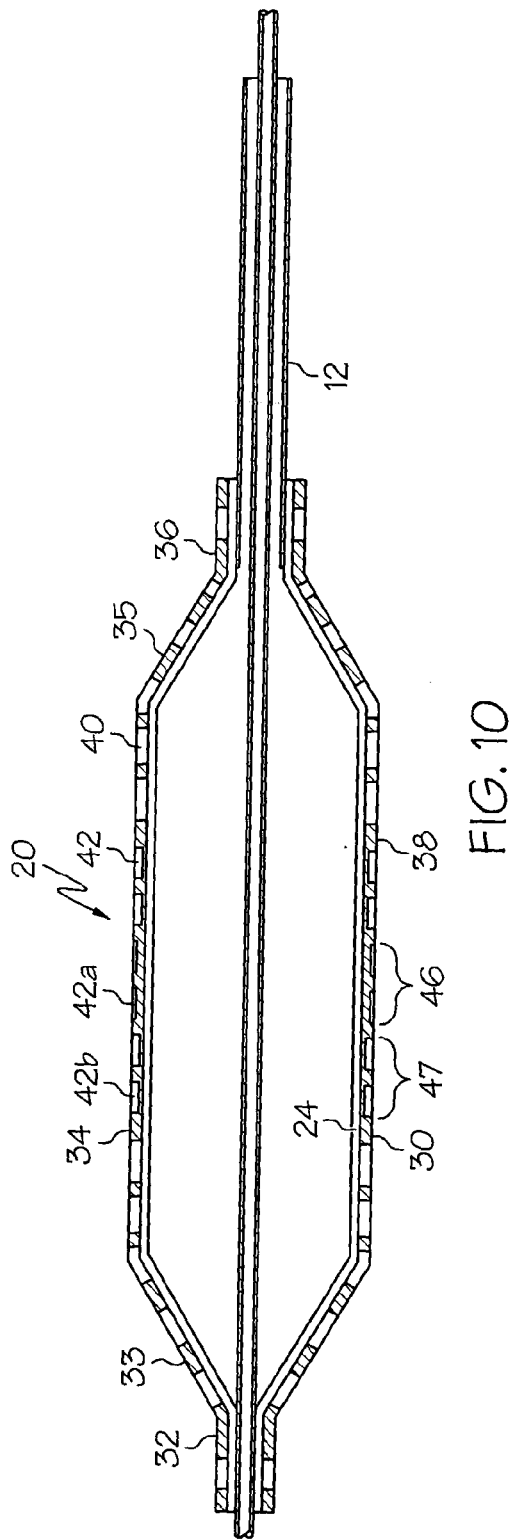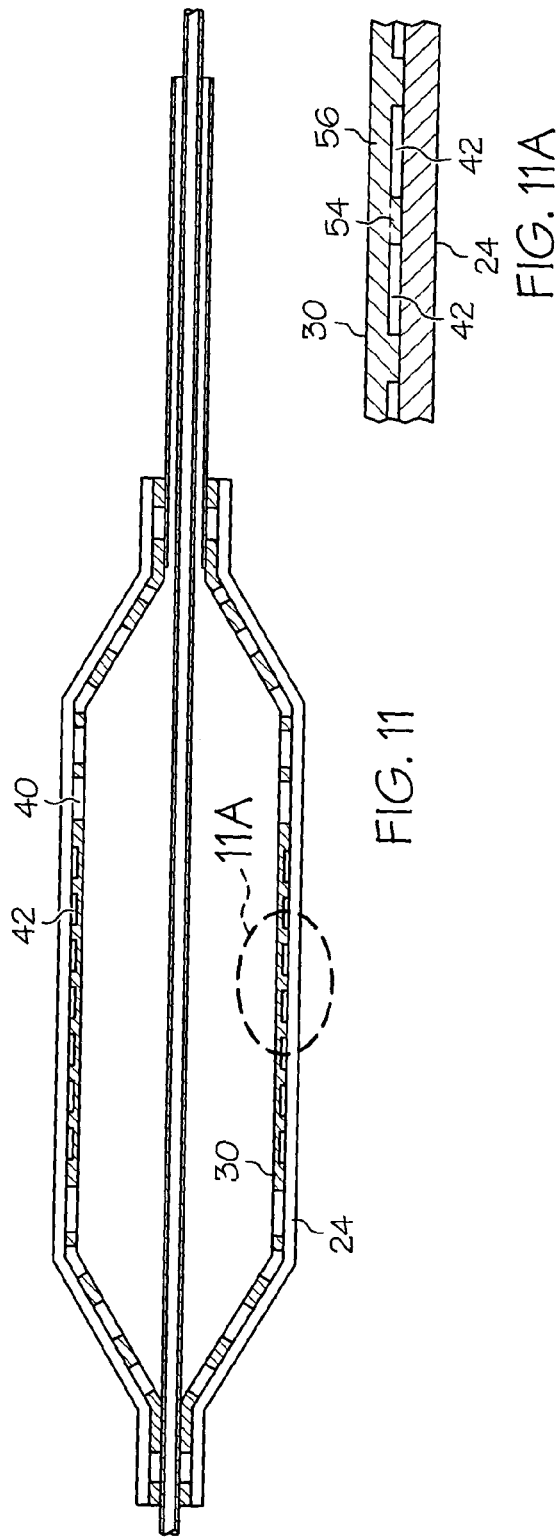

COMPOSITE BALLOON

BACKGROUND OF THE INVENTION

Medical devices comprising catheter shafts and catheter balloons are used in a variety of applications, such as vascular dilatation, stent delivery, drug delivery, delivery and operation of sensors and surgical devices such as blades, and the like. Desirable properties for balloons used in these devices varies according to the specific application, but for many procedures a high strength balloon is necessary, while softness, minimal deflated profile and tractability properties are highly desirable.

Commercial high strength balloons having wall strengths in excess of 20,000 psi have been formed of a wide variety of polymeric materials, including PET, nylons, polyurethanes and various block copolymer thermoplastic elastomers. U.S. Pat. No. 4,490,421, Levy, and U.S. Pat. No. 5,264,260, Saab, describe PET balloons. U.S. Pat. No. 4,906,244, Pinchuk et al., and U.S. Pat. No. 5,328,468, Kaneko, describe polyamide balloons. U.S. Pat. No. 4,950,239, Gahara, and U.S. Pat. No. 5,500,180, Anderson et al. describe balloons made from polyurethane block copolymers. U.S. Pat. No. 5,556,383, Wang et al., and U.S. Pat. No. 6,146,356, Wang et al., describe balloons made from polyether-block-amide copolymers and polyester-block-ether copolymers. U.S. Pat. No. 6,270,522, Simhambhatla, et al., describes balloons made from polyester-block-ether copolymers of high flexural modulus. U.S. Pat. No. 5,344,400, Kaneko, describes balloons made from polyarylene sulfide. U.S. Pat. No. 5,833,657, Reinhart et al, describes balloons having a layer of polyetheretherketone. All of these balloons are produced from extruded tubing of the polymeric material by a blow-forming radial expansion process. U.S. Pat. No. 5,250,069, Nobuyoshi et al., U.S. Pat. No. 5,797,877, Hamilton et al., and U.S. Pat. No. 5,270,086, Hamlin, describe still further materials which may be used to make such balloons.

There remains a need for novel balloon designs that are sufficiently flexible to traverse a tortuous anatomy while also having sufficient strength to withstand higher inflation pressures.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a catheter comprises a catheter shaft and an inflation balloon. The inflation balloon comprises a proximal cone, a distal cone and a body portion. The inflation balloon further comprises a body layer and a reinforcing layer, and the body layer is oriented radially outwardly from the reinforcing layer. The reinforcing layer further comprises a plurality of apertures.

In at least one other embodiment, the invention is directed to a catheter comprising a catheter shaft and an inflation balloon. The inflation balloon comprises a proximal cone, a distal cone and a body portion. The inflation balloon further comprises a body layer and a reinforcing layer, wherein the reinforcing layer is oriented about the body layer. The reinforcing layer comprises a single layer network of reinforcing material having a plurality of apertures, each aperture extending a full radial dimension of the reinforcing layer.

In at least one other embodiment, a catheter comprises a catheter shaft and an inflation balloon. The inflation balloon comprises a proximal cone portion, a distal cone portion and a body portion. The inflation balloon further comprises a body layer and a reinforcing layer, the reinforcing layer having a radial dimension oriented in a radial direction of the balloon. The reinforcing layer has a plurality of cavities extending radially into the reinforcing layer, at least a portion of the cavities having a radial dimension that is less than the radial dimension of the reinforcing layer.

In at least one embodiment, a method of making a catheter balloon comprises providing a perforated reinforcing tube, the perforated reinforcing tube comprising a wall portion and a plurality of perforations, the perforations extending radially into the wall portion; providing a parison; orienting the reinforcing tube and parison coaxially to form a balloon preform and orienting the balloon preform within a mold; and molding said balloon preform to form a composite balloon having a reinforcing layer.

In at least one other embodiment, a method of making a catheter balloon comprises providing a perforated reinforcing tube, the perforated reinforcing tube comprising a wall portion and a plurality of perforations, the perforations extending radially into the wall portion, the perforated reinforcing tube having a diameter approximately equal to a finished diameter of the eventual catheter balloon being made; providing a parison; providing a mold; lining the mold with said perforated reinforcing tube; orienting the parison within the mold, the parison oriented within the perforated reinforcing tube; and molding parison to form a composite balloon having a reinforcing layer. In some embodiments, the step of providing a perforated reinforcing tube further comprises providing a reinforcing tube; and forming a plurality of perforations in a surface of the reinforcing tube, the perforations extending radially into the reinforcing tube. In some embodiments, perforations are formed in the reinforcing tube by laser ablation.

In at least one other embodiment, a method of making a catheter balloon comprises providing a perforated reinforcing tube, the perforated reinforcing tube comprising a wall portion and a plurality of perforations, the perforations extending radially into the wall portion, the perforated reinforcing tube having a diameter approximately equal to a finished diameter of the eventual catheter balloon being made; providing an inflatable catheter balloon; orienting the inflatable catheter balloon within the reinforcing tube; inflating said catheter balloon such that an outer surface of the catheter balloon abuts an inner surface of the perforated reinforcing tube; and securing the perforated reinforcing tube to the catheter balloon to form a composite balloon having a reinforcing layer.

These and other embodiments which characterize the invention are pointed out with particularity in the claims annexed hereto and forming a part hereof However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 8 depicts another embodiment of a method of making a balloon.

FIG. 9 shows a cross-sectional view of another embodiment of a reinforcing tube.

FIG. 10 shows a sectional view of another embodiment of a reinforced balloon.

FIG. 11 shows a sectional view of another embodiment of a reinforced balloon. FIG. 11A shows a portion of FIG. 11 in greater detail.

DETAILED DESCRIPTION OF THE INVENTION

Figure 1:
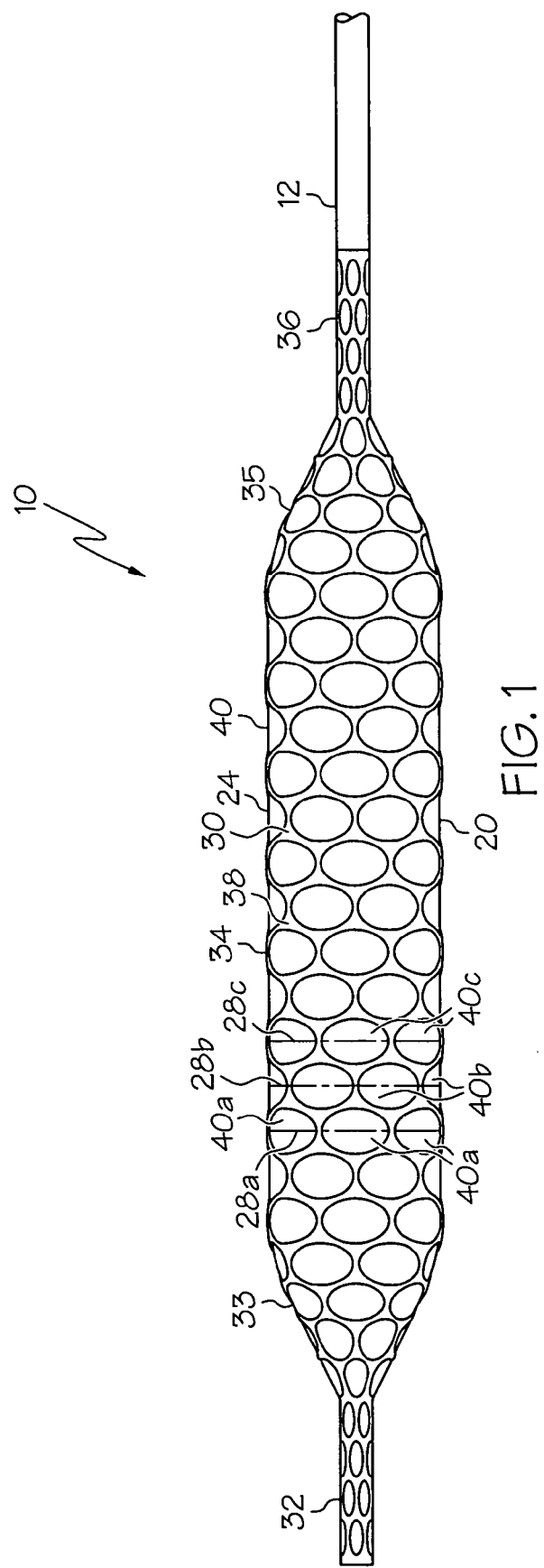
FIG. 1 shows a side view of an embodiment of a reinforced balloon.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
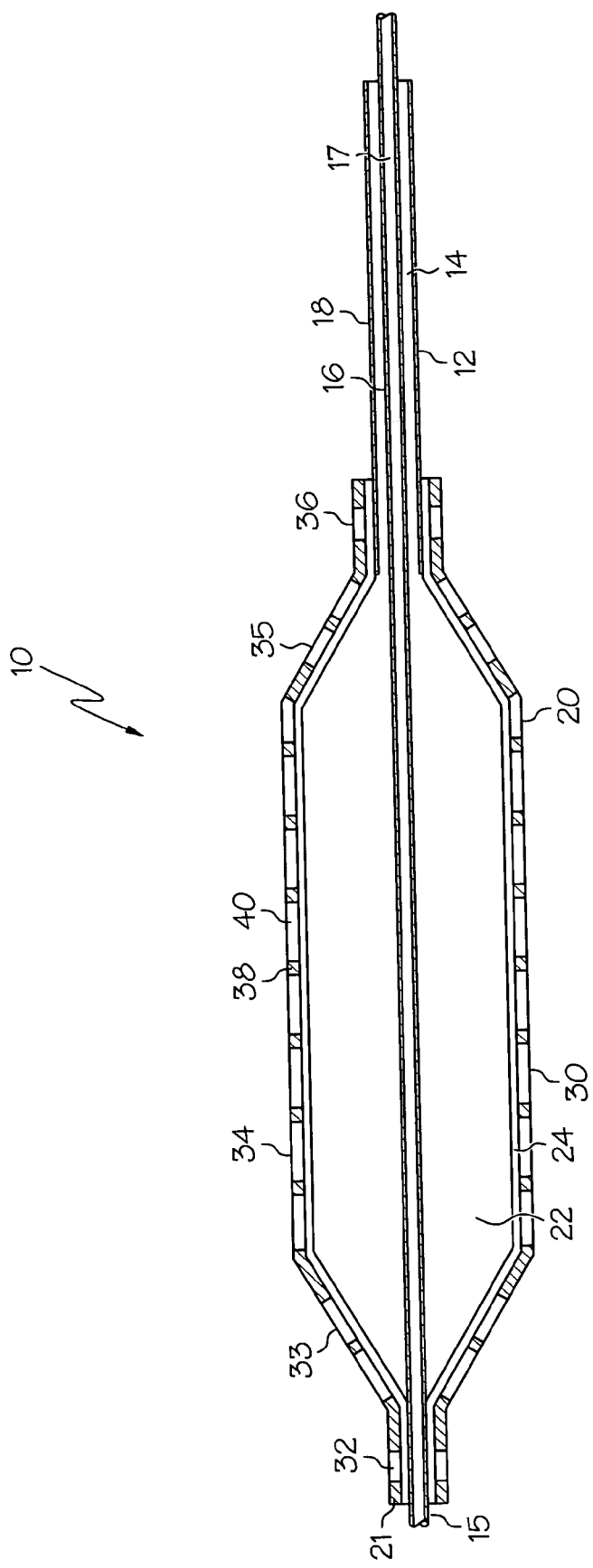
FIG. 2 shows a sectional view of an embodiment of a reinforced balloon.

FIGS. 1 and 2 show an embodiment of a balloon catheter or stent delivery system 10 having a catheter shaft 12 and a reinforced balloon 20. The balloon 20 may have a distal waist portion 32, a distal cone portion 33, a proximal cone portion 35, a proximal waist portion 36 and a body portion 34 which may be substantially cylindrical along its length.

The catheter shaft 12 may comprise any suitable catheter structure and may have an inflation lumen 14 in fluid communication with an interior portion 22 of the balloon 20. In some embodiments, the catheter shaft 12 may comprise an inner shaft 16 and an outer shaft 18 which may be coaxially aligned. The inner shaft 16 may further comprise a guidewire lumen 17. A distal end 15 of the inner shaft 16 may extend distal to a distal end 21 of the balloon 20. The distal waist 32 of the balloon 20 may be attached to a distal portion of the inner shaft 16. The proximal waist 36 of the balloon 20 may be attached to a distal portion 19 of the outer shaft 18. A proximal end of the catheter shaft 12 (not shown) may be arranged for an over-the-wire type guidewire system, a rapid-exchange type guidewire system, or any other suitable guidewire system.

The balloon 20 may further comprise a composite structure having a first or body layer 24 and a second or reinforcing layer 30. The reinforcing layer 30 may be oriented about the body layer 24. The reinforcing layer 30 may comprise a continuous single layer structural network 38 and a plurality of voids, such as cells or apertures 40. When the reinforcing layer 30 is described as being a continuous layer, it is intended that the reinforcing layer 30 is not made from overlapping fibers. Each aperture 40 may extend through a full radial dimension of the reinforcing layer 30. The structural network 38 desirably imparts greater strength to the balloon 20 while having a minimal impact on the folded profile of the balloon or flexibility in bending along its length.

The reinforcing layer 30 may have any suitable structural network 38 configuration. Thus, the apertures 40 may have any suitable size and shape. Apertures 40 may all have a similar shape, or in some embodiments, various apertures 40 may have different shapes. Some embodiments of apertures 40 may have continuous curvature, such as having circular or oval shapes. Some embodiments of apertures 40 may be polygonal, for example having triangular, square, rectangular or diamond shapes. In some embodiments, apertures 40 may change shape as the balloon 20 is traversed from the distal waist 32 to the proximal waist 36. In some embodiments, all of the apertures 40 which are entirely located on the balloon body portion 34 may comprise a similar shape.

In some embodiments, pluralities of apertures 40 may form rows or columns Various rows or columns of apertures 40 may be spaced along the length of the balloon 20 or about the circumference of the balloon 20. In some embodiments, various rows of apertures 40 may be staggered or offset from other rows. In some embodiments, apertures 40 may be oriented in various repeating patterns, for example in patterns similar to dimples in the surface of a golf ball.

Referring to FIG. 1, in some embodiments, a first plurality of apertures 40a may all be aligned about a first circumferential axis 28a of the balloon 20. A second plurality of apertures 40b may all be aligned about a second circumferential axis 28b of the balloon 20. The first circumferential axis 28a may be offset along the length of the balloon 20 from the second circumferential axis 28b. Apertures included in the first plurality of apertures 40a may be longitudinally and circumferentially offset from apertures included in the second plurality of apertures 40b. In some embodiments, the centroid of a first aperture 40a may be longitudinally aligned with the midpoint of a line extending between the centroids of two adjacent second apertures 40b. A third plurality of apertures 40c may all be aligned about a third circumferential axis 28c of the balloon 20. Apertures included in the third plurality of apertures 40c may be longitudinally aligned with apertures included in the first plurality of apertures 40a.

Figure 3:
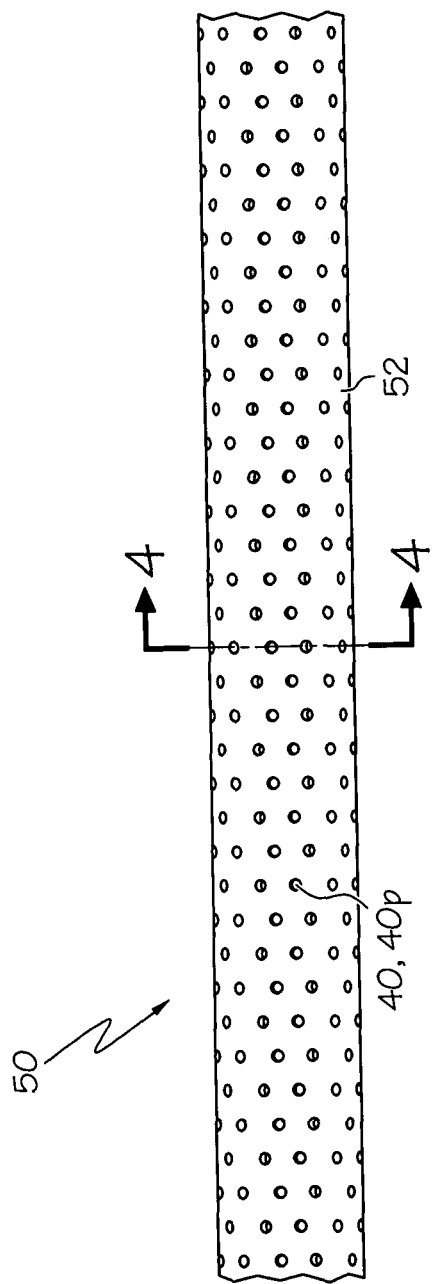
FIG. 3 shows a side view of an embodiment of a reinforcing tube.
Figure 4:
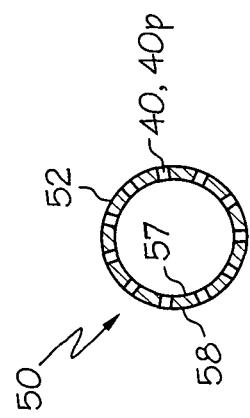
FIG. 4 shows a sectional view of the reinforcing tube of FIG. 3, taken across line 4-4 of FIG. 3.

FIGS. 3 and 4 show an embodiment of a perforated reinforcing sleeve or tube 50. In some embodiments, the reinforcing tube 50 may comprise a precursor to the reinforcing layer 30 (see FIG. 1) of the balloon 20.

The reinforcing tube 50 may generally comprise a cylindrical wall portion 52 having an inner surface 57 and an outer surface 58. A plurality of apertures 40 or aperture precursor holes 40p may be distributed in any suitable pattern across the surface of the reinforcing tube 50.

The reinforcing tube 50 may comprise any material suitable for use in a balloon that may be attached to the balloon body layer 24 (see FIG. 2). For example, in some embodiments, the reinforcing tube 50 may comprise PET, PEN, PBT, polyether-block-amide, nylons such as nylon 12, etc. In some embodiments, the reinforcing tube 50 may comprise the same material as the body layer 24 of the balloon 20. In some embodiments, the reinforcing tube 50 may comprise a material that is less compliant or that has a higher tensile yield strength than the material of the balloon body layer 24.

Apertures 40 or precursor holes 40p may be formed in the wall portion 52 using any suitable method. In some embodiments, the apertures 40 or precursor holes 40p may be drilled, notched, punched, abrasively machined, water jet machined, computer-numeric-control (CNC) machined, laser ablated, chemically dissolved, etc.

The reinforcing tube 50 or reinforcing layer 30 (see FIG. 1) may be secured to the balloon body layer 24 using any suitable method. In some embodiments, adhesives may be used, such as urethane and/or nylon based hot melts, UV activated adhesives, urethane based 2-part adhesives, epoxies, etc. In some embodiments, heat bonding may be used. In some embodiments, the reinforcing layer 30 may become attached to the body layer 24 during a molding process. Various embodiments of a reinforcing tube 50 may be used with various embodiments of balloon body layers 24 or parisons (balloon body layer precursors) to produce a reinforced composite balloon using various suitable methods. The balloon body layers 24 or parisons provided may comprise any suitable balloon material, such as thermoplastic polymeric materials, polyolefins, polyvinyl chloride, polyethylene terephthalate, polyamides, polyetheramides, polyurethanes, etc., as well as materials in U.S. Pat. No. 6,086,556 to Hamilton et al., U.S. Pat. No. 5,948,345 to Patel et al. and U.S. Pat. No. 5,792,415 to Hijlkema, the entire contents of which are hereby incorporated herein by reference in their entireties.

Figure 5:
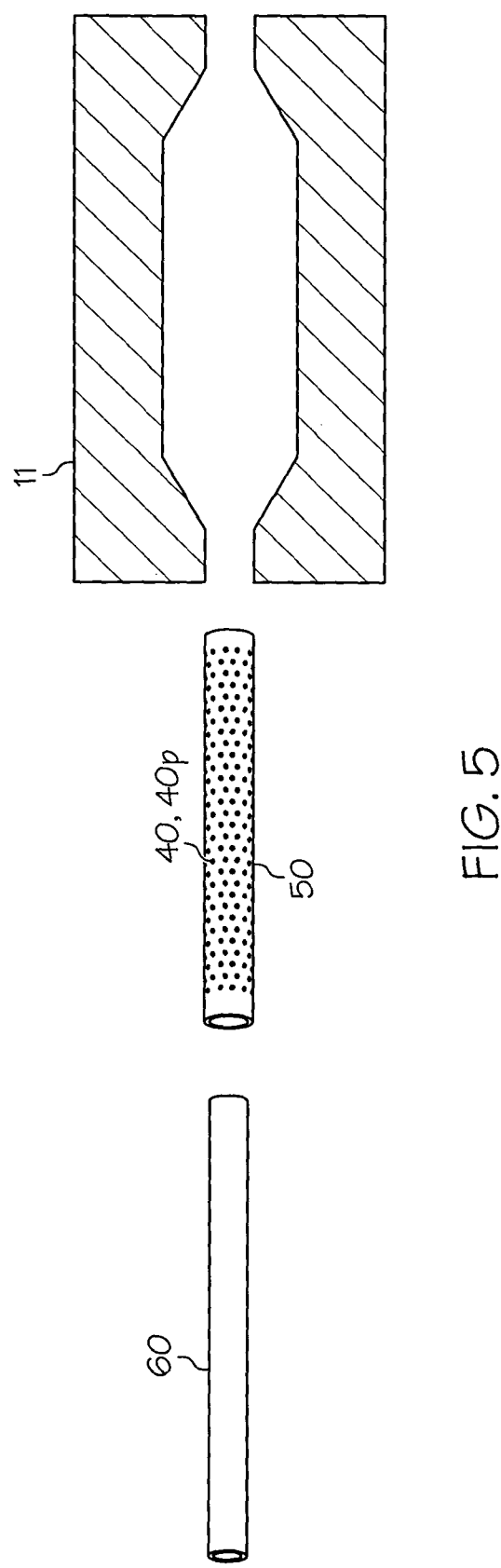
FIG. 5 depicts an embodiment of a method of making a balloon.

Referring to FIG. 5, a parison 60, a reinforcing tube 50 and a balloon mold 11 are depicted. The parison 60 and mold 11 may comprise any suitable materials and structure for molding an inflation balloon, for example as described in U.S. Pat. No. 5,948,345 to Patel et al. and U.S. Pat. No. 5,792,415 to Hijlkema.

The reinforcing tube 50 may be provided having any suitable combination of apertures 40 or precursor holes 40p. The parison 60 and the reinforcing tube 50 may be oriented coaxially, for example with the reinforcing tube 50 oriented about the parison 60, to form a balloon preform. The balloon preform may be placed within the mold 11. In some embodiments, the inner diameter of the reinforcing tube 50 may be equal to or slightly larger than the outer diameter of the parison 60. The combination reinforcing tube 50 and parison 60 may then be molded to form a reinforced composite balloon 20.

During molding, the parison 60 may be drawn to form the body layer 24 of the balloon 20, and the reinforcing tube 50 may be drawn to form the reinforcing layer 30 (see FIG. 1). Both the body layer 24 material and the reinforcing layer 30 material may experience strain, elongation and/or biaxial orientation during the molding process. Precursor holes 40p in the reinforcing tube 50 may change size and shape as the reinforcing tube 50 is molded to become the reinforcing layer 30 and the precursor holes 50 transition into apertures 40 in the reinforcing layer 30. In some embodiments, the body layer 24 and reinforcing layer 30 may be fused or bonded together during the molding process.

In some embodiments, molding may comprise creating a pressure differential between an internal cavity of the balloon preform and an area outside the balloon preform. Molding may further comprise the application of heat. In some embodiments, molding may be accomplished according to the processes disclosed in U.S. Pat. No. 6,124,007 to Wang et al. or U.S. Pat. No. 5,587,125 to Roychowdhury, which discuss molding balloons from multiple coaxial parisons, the entire contents of which are hereby incorporated herein by reference in their entireties.

In some embodiments, coating materials may be provided between the reinforcing tube 50 and parison 60 during molding to encourage bonding. Coatings may comprise adhesives, polymers similar to the parison 60 material, or any other suitable coating to encourage bonding or fusing between the parison 60 and reinforcing tube 50.

In some alternative embodiments, a molding process as described above may be used, and the positioning of the reinforcing tube 50 and parison 60 may be reversed. Thus, the reinforcing tube 50 and parison 60 may be oriented coaxially with the parison 60 oriented about the reinforcing tube 50. The eventual composite balloon 20 will comprise an outer body layer 24 and an inner reinforcing layer 30.

Figure 6:
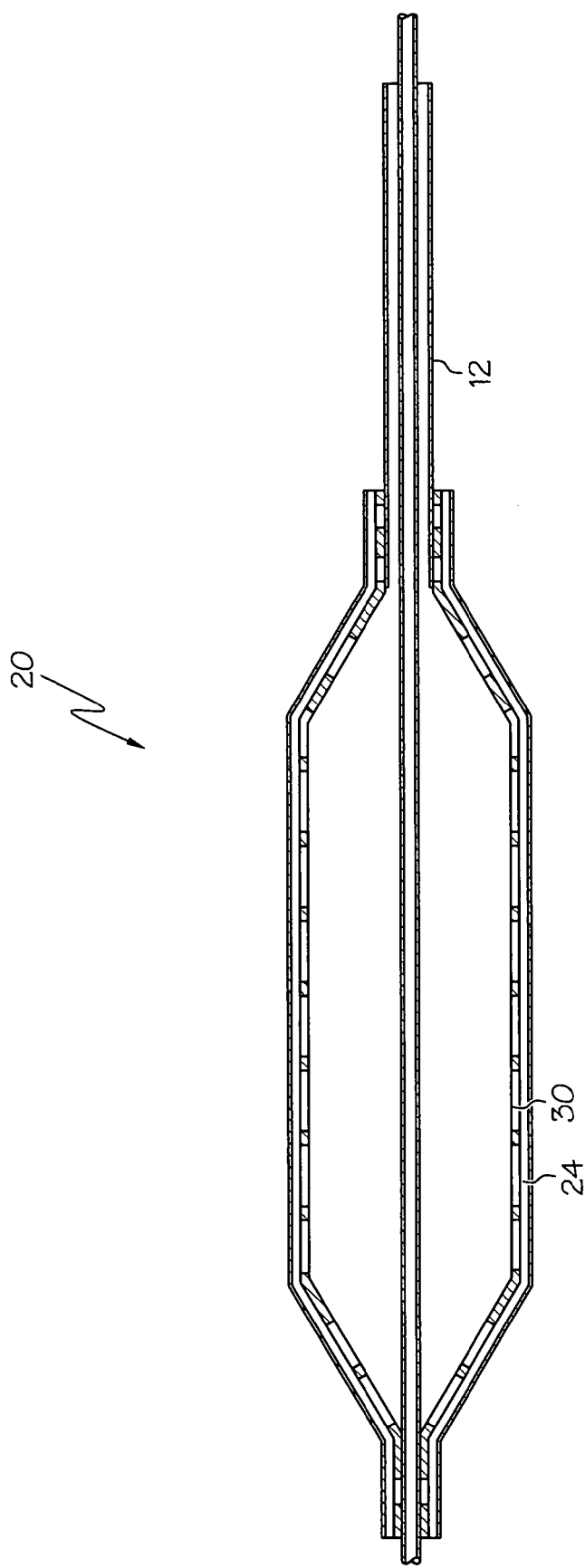
FIG. 6 shows a sectional view of another embodiment of a reinforced balloon.

FIG. 6 shows a sectional view of an embodiment of a reinforced balloon 20 wherein the reinforcing layer 30 is oriented within the body layer 24.

Figure 7:
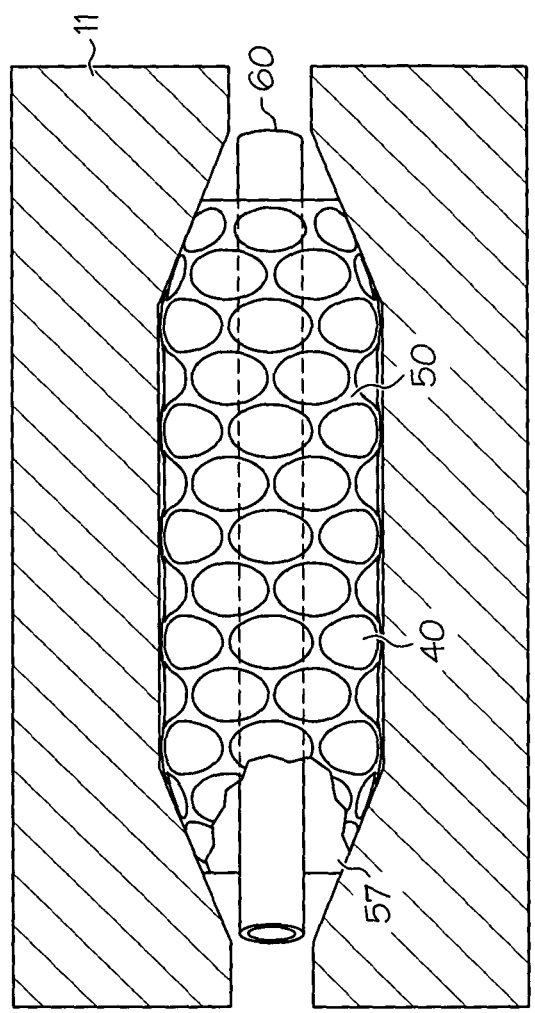
FIG. 7 depicts another embodiment of a method of making a balloon.

FIG. 7 shows another embodiment of a reinforcing tube 50, a parison 60 and a mold 11. The reinforcing tube 50 may be provided at a diameter substantially equal to an inflated diameter of the eventual composite balloon being molded. The reinforcing tube 50 may be provided with apertures 40 in any suitable pattern.

The reinforcing tube 50 may be placed inside the mold 11, and may be oriented to line the inner surface of the mold 11. The parison 60 may be placed within the mold and desirably oriented coaxially with the reinforcing tube 50 liner. The parison 60 may then be molded to form the body layer 24. During molding, the parison 60 may expand and eventually contact the inner surface 57 of the reinforcing tube 50. The reinforcing tube 50 and body layer 24 may bond together and form a composite balloon.

FIG. 8 depicts another method of making an embodiment of a reinforced balloon 20. A reinforcing tube 50 and any suitable balloon 13 may be provided. The reinforcing tube 50 may comprise a continuous single layer structural network 38 and a plurality of apertures 40. The balloon 13 may be oriented coaxially within the reinforcing tube 50 and inflated. The diameter of the reinforcing tube 50 may be substantially equal to an inflated diameter of the balloon 13. The outer surface of the balloon 13 may expand against the inner surface 57 of the reinforcing tube 50. The reinforcing tube 50/reinforcing layer 30 may be attached to the balloon 13 using any suitable method, such as laser welding, ultrasonic welding, heat bonding, thermal fusing, adhesives such as urethane and/or nylon based hot melts, UV activated adhesives, urethane based 2-part adhesives, epoxies, etc.

FIG. 9 shows a cross-sectional view of another embodiment of a reinforcing tube 50. Rather than having apertures which pass through the entire radial dimension of the wall 52, voids in the reinforcing tube 50 may comprise a plurality of blind holes or cavities 42 which pass through a portion of the wall 52 thickness.

Cavities 42 may have any suitable size, shape, quantity and distribution on the reinforcing tube 50. Any teaching with respect to apertures 40 (see FIG. 4) discussed herein may generally be applied to perforations 42.

In some embodiments, cavities 42 may extend from the outer surface 58 of the reinforcing tube 50 inwardly through any suitable portion of the wall 52 thickness. In some embodiments, a cavities 42 may be shallow. In some embodiments, a cavity 42 may be deep and may extend through a substantial portion of the wall 52 thickness.

Various embodiments of cavities 42 may be included on a single reinforcing tube 50. Further, in some embodiments, a reinforcing tube 50 may comprise at least one cavity 42 and at least one aperture 40.

In some embodiments, a reinforcing tube may have cavities 42 oriented on an inner surface of the tube 50. Inner cavities can be made by any suitable method, such as by laser ablation, abrasive water jet, masking and chemical dissolution etc. In some embodiments, a reinforcing tube may have cavities 42 oriented on both inner and outer surfaces of the tube 50. Any embodiment of a reinforcing tube 50 may be oriented either about or within a parison 60 for molding.

FIG. 10 shows an embodiment of a reinforced balloon 20 comprising a body layer 24 and a reinforcing layer 30. The reinforcing layer 30 may be oriented about the body layer 24. The reinforcing layer 30 may comprise a continuous structural network 38 and may include a plurality of apertures 40 and/or a plurality of cavities 42. Cavities 42 may extend into the reinforcing layer 30 from an outer surface of the balloon 20.

The balloon 20 may comprise at least one first cavity 42*a* of a first depth and at least one second cavity 42*b* of a second depth. The balloon 20 may further comprise a first area 46 having a plurality of first cavities 42*a* and a second area 47 having a plurality of second cavities 42*b*.

The distribution of apertures 40 and cavities 42 across the balloon 20 may be selected to impart greater strength to the balloon 20 at various locations. An area of the reinforcing layer 30 having cavities 42 will generally have more reinforcing material than an equal area having apertures 40, assuming a similar size, shape and distribution of cavities 42 and apertures 40, and will therefore provide greater strength to the balloon 20.

In some embodiments, apertures 40 may be provided in the reinforcing layer 30 in the distal waist 32, distal cone 33, proximal cone 35 and proximal waist 36 portions. Some apertures 40 may further be provided at the outer ends of the body portion 34. Cavities 42 may be provided on the body portion 34, and the depth of the cavities 42 may change toward the center of the body portion 34. For example, first cavities 42*a*, which may be the shallowest cavities 42, may be located near the center of the body portion 34. Second cavities 42*b*, which may be deeper than the first cavities 42*a*, may be located between the first cavities 42*a* and the ends of the body portion 34.

Various embodiments of a balloon 20 may include any suitable distribution of apertures 40 and cavities 42. In some embodiments, a first section of the reinforcing layer 30 may comprise apertures 40, and a second section of the reinforcing layer 30 may comprise cavities 42.

FIGS. 11 and 11A show another embodiment of a reinforced balloon 20 comprising a body layer 24 and a reinforcing layer 30. The body layer 24 may be oriented about the reinforcing layer 30. The reinforcing layer 30 may include a plurality of apertures 40 and a plurality of cavities 42. Cavities 42 may extend from an inner surface 25 of the body layer 24 into a portion of the reinforcing layer 30.

A reinforcing layer 30 having cavities 42 may further comprise a perforated portion 54 or perforated layer and an unperforated portion 56 or unperforated layer. Cavities 42 may extend through an entire radial dimension of the perforated portion 54. In some embodiments, the perforated portion 54 may be oriented between the unperforated portion 56 and the body layer 24.

Figure 12:
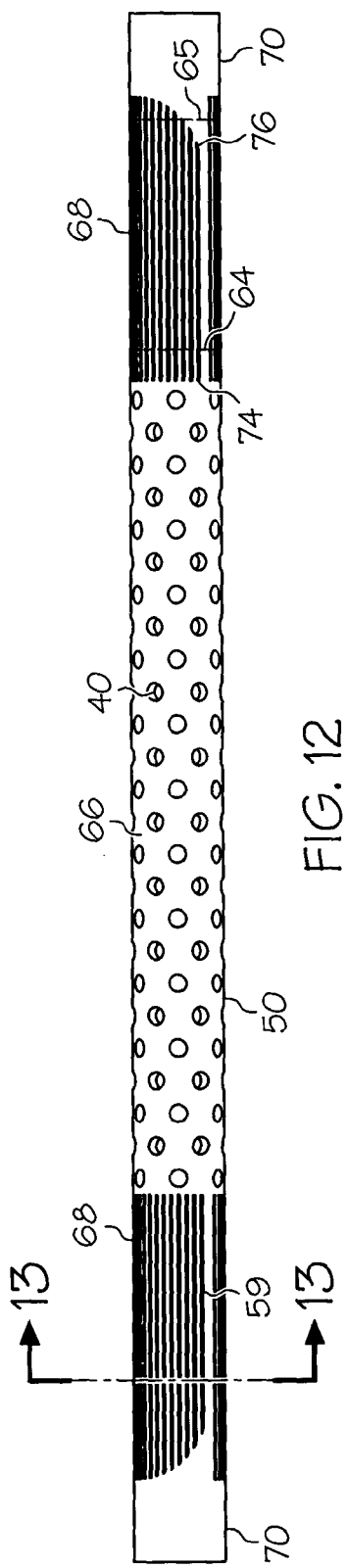
FIG. 12 shows a side view of another embodiment of a reinforcing tube.
Figure 13:
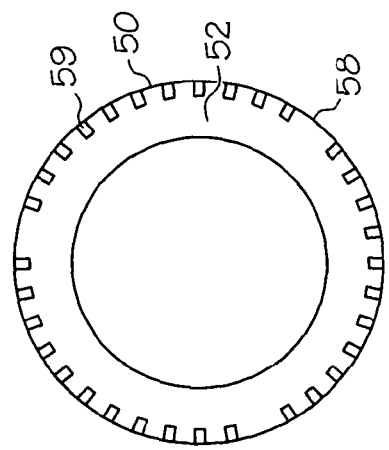
FIG. 13 shows a sectional view of the reinforcing tube of FIG. 12, taken across line 13-13 of FIG. 3.

FIGS. 12 and 13 show another embodiment of a reinforcing tube 50 which may include a plurality of apertures 40. The tube 50 may comprise a central portion 66 which may eventually comprise the body portion 24 (see FIG. 1) of a balloon 20. The tube may further comprise intermediate portions 68, which may eventually comprise a cone portion 33, 35 of a balloon 20, and end portions 70, which may eventually comprise a waist portion 32, 36 of a balloon 20.

The intermediate portions 68 of the reinforcing tube 50 may comprise a plurality of channels or slits 59. Each slit 59 may span a portion of the length of the reinforcing tube 50. Each slit 59 may extend from an outer surface 58 of the tube 50 to any suitable distance into the wall 52 of the tube. A slit 59 may have any suitable cross-sectional shape.

In some embodiments, a slit 59 may span the entire length of an intermediate portion 68, or may extend into another portion of the tube 50. In some embodiments, a plurality of slits 59 may each be oriented with a first or inner end 74 located at a boundary between an intermediate portion 68 and the central portion 66, and may extend into the intermediate portion 68. The various slits 59 may terminate at a second or outer end 76 located various distances away from the inner end 74. Thus, in some embodiments, a circumference 64 of an intermediate portion 68 located near the central portion 66 may include more slits 59 than another circumference 65 of the intermediate portion 68 located near an end portion 70. This may be desirable in various embodiments which are molded to form the composite balloon 20, as the circumference 64 will generally experience a greater amount of strain and elongation than the second circumference 65 as the intermediate portion 68 is molded to form a cone portion 33, 35 of the balloon 20.

Figure 14:
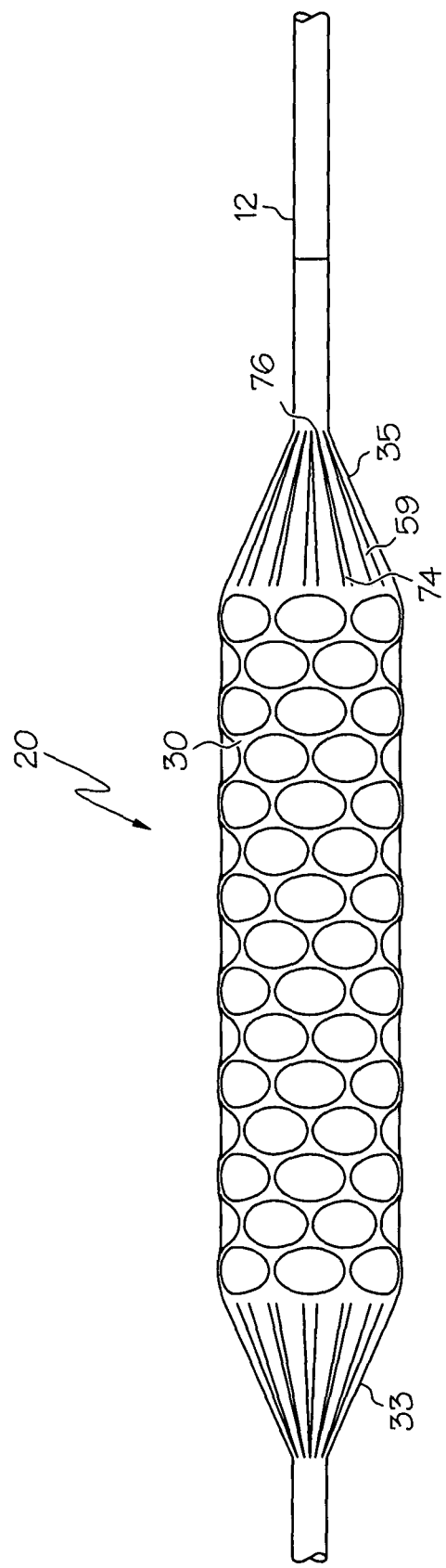
FIG. 14 shows a side view of another embodiment of a balloon.

FIG. 14 shows an embodiment of a reinforced balloon 20 having a reinforcing layer 30 molded from a reinforcing tube having slits 59, for example as shown in FIGS. 12 and 13. As the reinforcing tube transitions into the reinforcing layer 30, the intermediate portions 68 (see FIG. 12) may transition into the proximal cone 35 and the distal cone 33. The slits 59 and the underlying reinforcing material oriented below and adjacent to the slits 59 may elongate as the diameter increases during molding. Material located towards the inner end 74 of a slit 59 may experience a greater amount of elongation than material located toward the outer end 76 of the slit 59.

Figure 15:
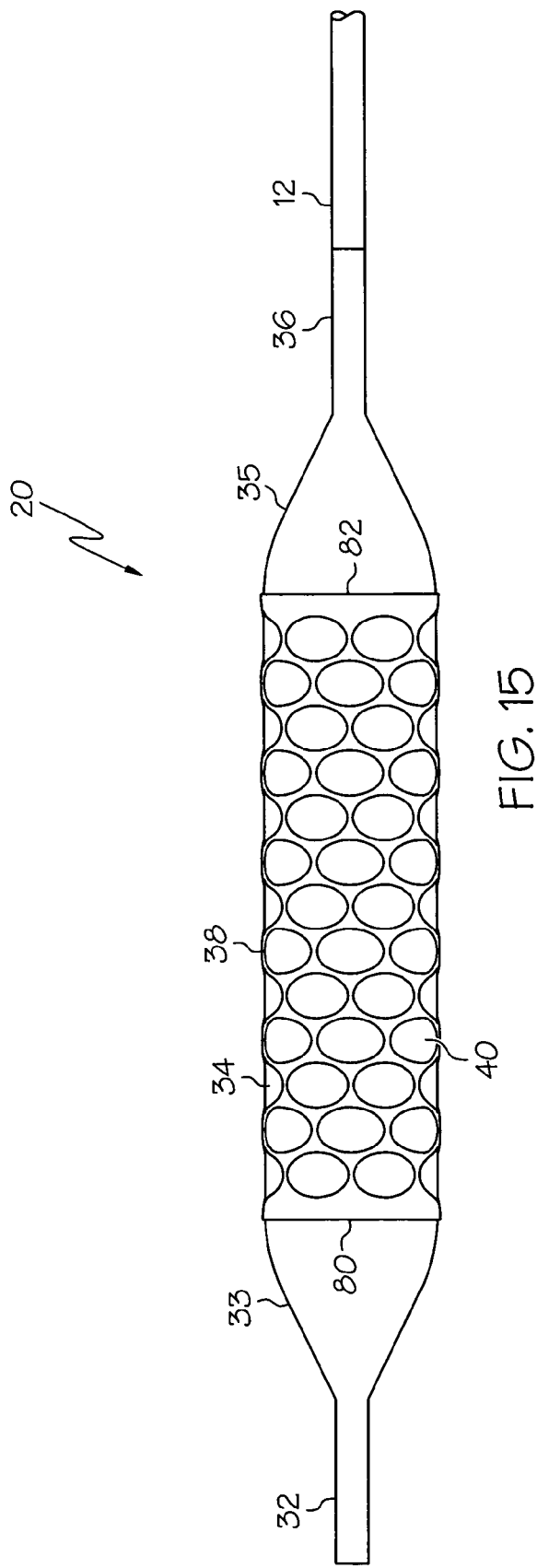
FIG. 15 shows a side view of another embodiment of a balloon.

FIG. 15 shows an embodiment of a reinforced balloon 20 having a reinforcing layer 30 that extends substantially the length of the body portion 34 of the balloon 20. A first end 80 of the reinforcing layer 30 may be oriented about the body portion 34 near the distal cone 33. A second end 82 of the reinforcing layer 30 may be oriented about the body portion 34 near the proximal cone 35.

Various embodiments of a reinforcing layer 30 may extend to any suitable portion of the balloon 20. In various embodiments, an end 80, 82 of the reinforcing layer 30 may be oriented about a balloon waist portion 32, 36, a balloon cone portion 33, 35 or anywhere along the length of the body portion 34. Such embodiments may be made using any suitable method, for example by providing a reinforcing tube 50 (see FIG. 4) of suitable length and molding the balloon 20 according to the methods disclosed herein.

Figure 16:
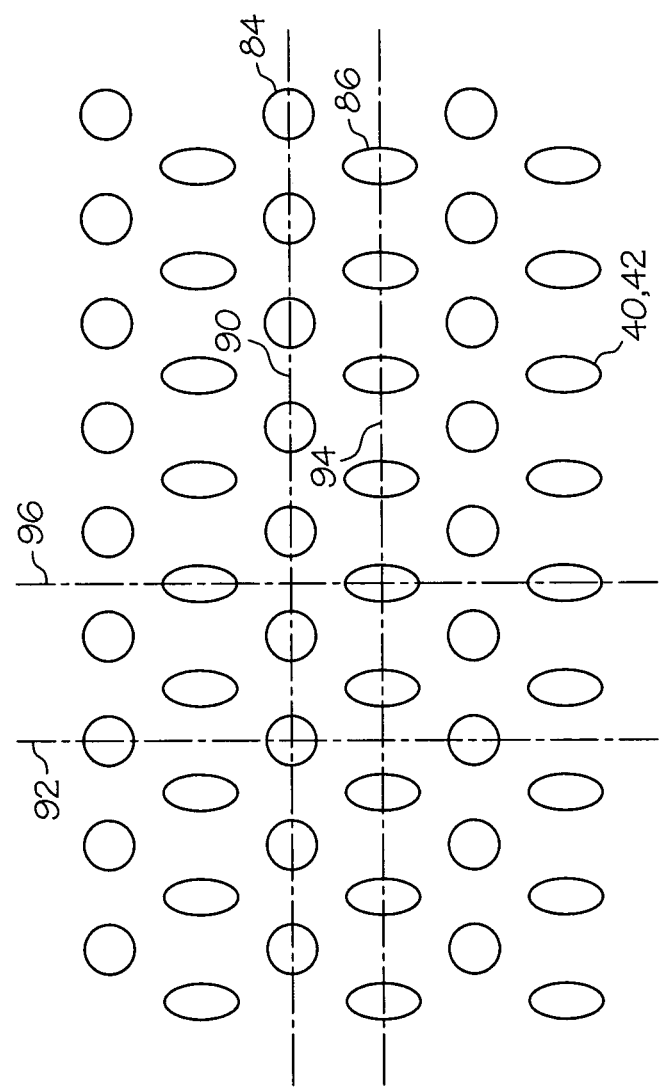
FIG. 16 shows a pattern for an embodiment of an aperture pattern.

FIG. 16 shows an embodiment of a flat pattern for apertures 40 and/or cavities 42 which may be used in a reinforcing layer 30, or in some embodiments, a reinforcing tube 50. The pattern may comprise a plurality of first apertures 84 and a plurality of second apertures 86. First apertures 84 may comprise any suitable size and shape. The first apertures 84 may be aligned in rows 90 and columns 92. Any suitable spacing between first apertures 84 may be used in the rows 90 and columns 92.

The second apertures 86 may comprise any suitable size and shape, and may be different in size and/or shape than the first apertures 84. The second apertures 86 may be aligned in rows 94 and columns 96. Any suitable spacing between second apertures 86 may be used in the rows 94 and columns 96. In some embodiments, the center-to-center spacing of first apertures 84 in a row 90 may be the same as the spacing of second apertures 86 in a row 94. Similarly, the spacing of first apertures 84 in a column 92 may be the same as the spacing of second apertures 86 in a column 96.

Rows 90 of first apertures 84 may be offset from rows 94 of second apertures 86. Columns 92 of first apertures 84 may be offset from columns 96 of second apertures 86.

While the pattern is described with respect to apertures 40, any suitable combination of apertures 40, cavities 42 or apertures 40 and cavities 42 may be used. Further, the various cavities 42 may be of any suitable depth. In some embodiment, first cavities may be deeper than second cavities. In some embodiments, the depth of first cavities and/or second cavities may vary across the pattern.

In some embodiments, a balloon 20 may comprise multiple body layers 24 and/or multiple reinforcing layers.

In some embodiments, a balloon 20 may be formed by first forming the balloon body 34 and then forming apertures 40 and/or cavities 42 in the reinforcing layer 30, for example by laser ablation, abrasive water jet, masking and chemical dissolution, etc.

In some embodiments, a balloon 20 may be formed using a layer-by-layer deposit process that uses electrostatic interaction between oppositely charged particle layers, for example as described in US Patent Application Publication Nos. 2010/0179645 and 2006/0212106, the entire disclosures of which are hereby incorporated herein by reference in their entireties. In some embodiments, various built-up layers may comprise body layers 24 and/or various built-up layers may comprise reinforcing layers 30. In some embodiments, a shaped reinforcing layer 30 may be built up by selective masking and use of a layer-by-layer deposit process.

In some embodiments, a balloon 20 may include surface features such as protrusions or a textured surface, for example as described in U.S. Pat. No. 6,258,099, U.S. Pat. No. 6,676,667, U.S. Pat. No. 6,736,841 and/or U.S. Pat. No. 6,786,889, the entire disclosures of which are hereby incorporated herein by reference in their entireties. The surface features may be formed using any suitable method.

Figure 17:
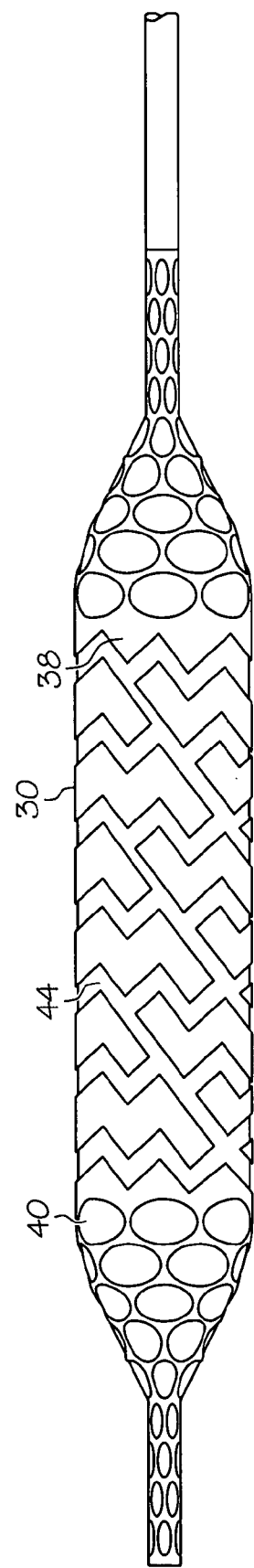
FIG. 17 shows a side view of another embodiment of a balloon.

Referring to FIG. 17, in some embodiments, a reinforcing layer 30 may have a shaped surface oriented to secure a stent. For example, shaped apertures 44 may be selectively shaped and oriented across the surface of a balloon 20 such that portions of a stent may sit within a shaped aperture 44 and/or portions of the structural network 38 may abut edges of the stent. As shown in FIG. 17, shaped apertures 44 for serpentine bands that extend around the balloon 20. Engagement between the reinforcing layer 30 and a stent may prevent the stent from translocating on the balloon before and/or during stent expansion. The reinforcing layer 30 may be designed to secure a stent during stent delivery and/or during balloon inflation. In some embodiments, the reinforcing layer 30 may be designed to secure a stent when the balloon is in a deflated and/or folded delivery configuration. In some embodiments, the reinforcing layer may be designed to continue securing a stent during balloon inflation.

In some embodiments, the pattern of the reinforcing layer 30 may impart varying amounts of strength to the balloon 20 along its length. In some embodiments, the reinforcing layer 30 may be selectively shaped to provide a balloon with compliance that varies, for example along the length of the balloon 20.

Some embodiments of balloons disclosed herein are suitable for use with stents or other expandable medical devices. Stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

Stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

Stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments a stent, the delivery system, balloon or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments, a balloon may include a coating, such as a lubricious coating. In some embodiments the at least a portion of a balloon or stent may be configured to include one or more mechanisms for the delivery of a therapeutic agent. Often the agent will be in the form of a coating or other layer (or layers) of material placed on a surface region of the balloon or stent, which is adapted to be released at the site of the stent's implantation or areas adjacent thereto. In some embodiments, coating material may be oriented within apertures 40 located on the surface of the balloon, or between layers of the balloon, such as between the body layer 24 and the reinforcing layer 30.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

In some embodiments, a balloon 20 may have apertures 40 in an outer reinforcing layer 30, for example as described according to the following paragraphs:

1. A catheter comprising:
a catheter shaft and an inflation balloon; the inflation balloon comprising a proximal cone, a distal cone and a body portion; the inflation balloon further comprising a body layer and a reinforcing layer; the reinforcing layer oriented about the body layer; the reinforcing layer comprising a single layer network of reinforcing material having a plurality of apertures; each aperture extending a full radial dimension of the reinforcing layer.
2. The catheter of paragraph 1, wherein each aperture comprises a shape having continuous curvature.
3. The catheter of paragraph 2, wherein each aperture comprises an oval shape.
4. The catheter of paragraph 1, wherein each aperture of the reinforcing layer located in said body portion comprises a similar shape.
5. The catheter of paragraph 1, wherein a plurality of apertures of the reinforcing layer located in said body portion are aligned in a circumferential direction of the inflation balloon.
6. The catheter of paragraph 5, wherein a second plurality of apertures of the reinforcing layer located in said body portion are aligned in a circumferential direction of the inflation balloon; apertures of the first plurality of apertures being longitudinally and circumferentially offset from apertures of the second plurality of apertures.
7. The catheter of paragraph 6, wherein a third plurality of apertures of the reinforcing layer located in said body portion are aligned in a circumferential direction of the inflation balloon; apertures of the first plurality of apertures being longitudinally aligned with apertures of the third plurality of apertures.
8. The catheter of paragraph 1, wherein the body layer and the reinforcing layer comprise the same material.
9. The catheter of paragraph 1, wherein the reinforcing layer comprises a material having a higher yield strength than the body layer.
10. The catheter of paragraph 1, wherein the shape of the apertures change geometry from the body portion to the distal cone portion.
11. The catheter of paragraph 1, comprising a first aperture of a first shape and a second aperture of a second shape that is different from the first shape.
12. The catheter of paragraph 11, wherein the first aperture and the second aperture are located on the body portion.
13. The catheter of paragraph 1, wherein a plurality of said apertures are oriented such that at least a portion of said reinforcing material abuts a side portion of a stent.
14. The catheter of paragraph 1, comprising at least one diamond-shaped aperture.
15. The catheter of paragraph 1, further comprising a drug coating.
16. The catheter of paragraph 15, wherein a portion of the drug coating is oriented within an aperture.
17. The catheter of paragraph 15, wherein a portion of the drug coating is oriented between the body layer and the reinforcing layer.
18. The catheter of paragraph 1, wherein said reinforcing layer comprises at least one slit located in the proximal cone portion.

In some embodiments, a balloon 20 may have an outer body layer 24 and an inner reinforcing layer 30, for example as described according to the following paragraphs:

19. A catheter comprising:
a catheter shaft and an inflation balloon; the inflation balloon comprising a proximal cone, a distal cone and a body portion; the inflation balloon further comprising a body layer and a reinforcing layer; the body layer oriented radially outwardly from the reinforcing layer; the reinforcing layer having a plurality of apertures.
20. The catheter of paragraph 19, wherein the reinforcing layer comprises a single layer network of reinforcing material having said plurality of apertures.
21. The catheter of paragraph 20, wherein said apertures pass through a full radial dimension of the reinforcing layer.
22. The catheter of paragraph 19, wherein each aperture of the reinforcing layer located in said body portion comprises a similar shape.
23. The catheter of paragraph 19, wherein a plurality of apertures of the reinforcing layer located in said body portion are aligned in a circumferential direction of the inflation balloon.
24. The catheter of paragraph 23, wherein a second plurality of apertures of the reinforcing layer located in said body portion are aligned in a circumferential direction of the inflation balloon; the first plurality of apertures being circumferentially offset from the second plurality of apertures.
25. The catheter of paragraph 24, wherein a third plurality of apertures of the reinforcing layer located in said body portion are aligned in a circumferential direction of the inflation balloon; the first plurality of apertures being circumferentially aligned with the third plurality of apertures.
26. The catheter of paragraph 19, wherein the body layer and the reinforcing layer comprise the same material.
27. The catheter of paragraph 19, wherein the reinforcing layer comprises a material that is less compliant than the body layer.
28. The catheter of paragraph 19, wherein the apertures change geometry from the body portion to the distal cone portion.
29. The catheter of paragraph 19, comprising a first aperture of a first shape and a second aperture of a second shape that is different from the first shape.
30. The catheter of paragraph 29, wherein the first aperture and the second aperture are located on the body portion.
31. The catheter of paragraph 19, wherein each aperture comprises a shape having continuous curvature.
32. The catheter of paragraph 31, wherein each aperture comprises an oval shape.
33. The catheter of paragraph 19, wherein said reinforcing layer comprises at least one slit located in the proximal cone portion.

In some embodiments, a balloon 20 may have a outer body layer 24 and a reinforcing layer 30 having partial depth cavities 42, for example as described according to the following paragraphs:

34. A catheter comprising:
a catheter shaft and an inflation balloon; the inflation balloon comprising a proximal cone portion, a distal cone portion and a body portion; the inflation balloon further comprising a body layer and a reinforcing layer, the reinforcing layer having a radial dimension oriented in a radial direction of the balloon; the reinforcing layer having a plurality of cavities extending radially into the reinforcing layer, at least a portion of the cavities having a radial dimension that is less than the radial dimension of the reinforcing layer.

35. The catheter of paragraph 34, wherein a plurality of cavities each comprise an oval shape.

36. The catheter of paragraph 34, wherein a plurality of cavities located in said balloon body portion comprise a similar shape.

37. The catheter of paragraph 34, wherein the body layer and the reinforcing layer comprise the same material.

38. The catheter of paragraph 34, wherein the shape of the cavities change from the body portion to the distal cone portion.

39. The catheter of paragraph 34, wherein the reinforcing layer is oriented about the body layer.

40. The catheter of paragraph 39, wherein the cavities extend into the reinforcing layer from an outer surface of the balloon.

41. The catheter of paragraph 39, wherein the reinforcing layer comprises a perforated portion and an unperforated portion, the cavities extending through a full radial dimension of the perforated portion.

42. The catheter of paragraph 34, wherein the body layer is oriented about the reinforcing layer.

43. The catheter of paragraph 42, wherein the cavities extend from an inner surface of the body layer into the reinforcing layer.

44. The catheter of paragraph 42, wherein the reinforcing layer comprises a perforated portion and an unperforated portion, the cavities extending through a full radial dimension of the perforated portion.

45. The catheter of paragraph 44, wherein the perforated portion is oriented between the unperforated portion and the body layer.

46. The catheter of paragraph 34, comprising at least one diamond-shaped cavity.

47. The catheter of paragraph 34, further comprising a drug coating.

48. The catheter of paragraph 47, wherein a portion of the drug coating is oriented within a cavity.

49. The catheter of paragraph 47, wherein a portion of the drug coating is oriented between the body layer and the reinforcing layer.

In some embodiments, a reinforced balloon 20 may be made according to a method using a perforated reinforcing tube which is molded to form a reinforcing layer 30, for example as described in the following paragraphs:

50. A method of making a catheter balloon comprising:
    providing a perforated reinforcing tube, the perforated reinforcing tube comprising a wall portion and a plurality of perforations, the perforations extending radially into the wall portion;
    providing a parison;
    orienting the reinforcing tube and parison coaxially to form a balloon preform and orienting the balloon preform within a mold;
    molding said balloon preform to form a composite balloon having a reinforcing layer.

51. The method of paragraph 50, wherein the step of molding comprises creating a pressure differential between an internal cavity of the balloon preform and an area outside the balloon preform.

52. The method of paragraph 50, wherein material of the reinforcing tube experiences strain during the step of molding.

53. The method of paragraph 50, wherein the step of providing a perforated reinforcing tube further comprises:
    providing a reinforcing tube; and
    forming a plurality of perforations in a surface of the reinforcing tube, the perforations extending radially into the reinforcing tube.

54. The method of paragraph 53, wherein the perforations are formed in the reinforcing tube by laser ablation.

55. The method of paragraph 50, wherein the perforated reinforcing tube is oriented within the parison.

56. The method of paragraph 50, wherein the parison is oriented within the perforated reinforcing tube.

57. The method of paragraph 50, wherein at least a portion of the perforations in the perforated reinforcing tube have a radial dimension that is less than a radial dimension of the wall portion.

58. The method of paragraph 50, wherein at least a portion of the perforations in the perforated reinforcing tube comprise apertures which extend through a full radial dimension of the wall portion.

59. The method of paragraph 50, wherein in the material of the reinforcing tube has a higher tensile strength than the material of the parison.

In some embodiments, a reinforced balloon 20 may be made using a relatively large diameter embodiment of a reinforcing tube 50, for example according to a method as described in the following paragraphs:

60. A method of making a catheter balloon comprising:
    providing a perforated reinforcing tube, the perforated reinforcing tube comprising a wall portion and a plurality of perforations, the perforations extending radially into the wall portion, the perforated reinforcing tube having a diameter approximately equal to a finished diameter of the eventual catheter balloon being made;
    providing a parison;
    providing a mold;
    lining the mold with said perforated reinforcing tube;
    orienting the parison within the mold, the parison oriented within the perforated reinforcing tube;
    molding parison to form a composite balloon having a reinforcing layer.

61. The method of paragraph 60, wherein the step of molding comprises creating a pressure differential between an internal cavity of the parison and an area outside the perforated reinforcing tube.

62. The method of paragraph 60, wherein in the material of the reinforcing tube has a higher tensile strength than the material of the parison.

63. The method of paragraph 60, wherein the step of providing a perforated reinforcing tube further comprises:
    providing a reinforcing tube; and
    forming a plurality of perforations in a surface of the reinforcing tube, the perforations extending radially into the reinforcing tube.

64. The method of paragraph 63, wherein the perforations are formed in the reinforcing tube by laser ablation.

65. The method of paragraph 60, wherein at least a portion of the perforations in the perforated reinforcing tube have a radial dimension that is less than a radial dimension of the wall portion.

66. The method of paragraph 60, wherein at least a portion of the perforations in the perforated reinforcing tube comprise apertures which extend through a full radial dimension of the wall portion.

In some embodiments, a reinforced balloon 20 may be made using a relatively large diameter embodiment of a reinforcing tube 50, for example according to a method as described in the following paragraphs:

67. A method of making a catheter balloon comprising:
    providing a perforated reinforcing tube, the perforated reinforcing tube comprising a wall portion and a plurality of perforations, the perforations extending radially into the wall portion, the perforated reinforcing tube having a diameter approximately equal to a finished diameter of the eventual catheter balloon being made;
    providing an inflatable catheter balloon;
    orienting the inflatable catheter balloon within the reinforcing tube;
    inflating said catheter balloon such that an outer surface of the catheter balloon abuts an inner surface of the perforated reinforcing tube; and
    securing the perforated reinforcing tube to the catheter balloon to form a composite balloon having a reinforcing layer.
68. The method of paragraph 67, wherein the perforated reinforcing tube to is secured to the catheter balloon using an adhesive.
69. The method of paragraph 67, wherein the perforated reinforcing tube to is secured to the catheter balloon via heat bonding.
70. The method of paragraph 67, wherein the step of providing a perforated reinforcing tube further comprises:
    providing a reinforcing tube; and
    forming a plurality of perforations in a surface of the reinforcing tube, the perforations extending radially into the reinforcing tube.
71. The method of paragraph 70, wherein the perforations are formed in the reinforcing tube by laser ablation.
72. The method of paragraph 67, wherein at least a portion of the perforations in the perforated reinforcing tube have a radial dimension that is less than a radial dimension of the wall portion.
73. The method of paragraph 67, wherein at least a portion of the perforations in the perforated reinforcing tube comprise apertures which extend through a full radial dimension of the wall portion.
74. The method of paragraph 67, wherein in the material of the reinforcing tube has a higher tensile strength than the material of the parison.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A catheter comprising:
   a catheter shaft and a balloon; the balloon comprising a proximal cone portion, a distal cone portion and a body portion; the balloon further comprising a body layer and a reinforcing layer, the body layer surrounding the reinforcing layer, the body layer and reinforcing layer contacting each other at least in the body portion when the balloon is inflated, the reinforcing layer having a thickness; the reinforcing layer having a plurality of voids arranged in a repeating pattern, said voids extending into the reinforcing layer, at least a portion of the voids comprising cavities having a depth that is less than the thickness of the reinforcing layer.
2. The catheter of claim 1, wherein a plurality of voids each comprise a shape having continuous curvature about its central axis.
3. The catheter of claim 1, wherein a plurality of voids located in said balloon body portion comprise a similar shape.
4. The catheter of claim 1, wherein the reinforcing layer comprises a material having a higher yield strength than the body layer.
5. The catheter of claim 1, comprising a first void of a first shape and a second void of a second shape that is different from the first shape, the first void and the second void located in the balloon body portion.
6. The catheter of claim 1, wherein the voids extend from an inner surface of the body layer into the reinforcing layer.
7. The catheter of claim 1, wherein a portion of said voids in the reinforcing layer each comprise an aperture, each aperture extending through the thickness of the reinforcing layer.
8. The catheter of claim 1, comprising a first cavity of a first depth and a second cavity of a second depth that is different from the first depth, the first cavity and the second cavity located in the balloon body portion.
9. The catheter of claim 1, wherein said reinforcing layer comprises at least one slit located in the proximal cone portion.
10. A catheter comprising:
    a catheter shaft and a balloon; the balloon comprising a proximal cone portion, a distal cone portion and a body portion; the balloon further comprising a body layer and a reinforcing layer, the reinforcing layer having a thickness; the reinforcing layer having a plurality of voids arranged in a repeating pattern, said voids extending into the reinforcing layer, at least a portion of the voids comprising cavities having a depth that is less than the thickness of the reinforcing layer;
    wherein the reinforcing layer surrounds the body layer.
11. The catheter of claim 10, further comprising a drug coating, wherein a portion of the drug coating is oriented within a void.
12. The catheter of claim 1, wherein a plurality of voids of the reinforcing layer located in said body portion are aligned in a circumferential direction of the balloon.
13. The catheter of claim 12, wherein a second plurality of voids of the reinforcing layer located in said body portion are aligned in a circumferential direction of the balloon; the first plurality of voids being circumferentially offset from the second plurality of voids.

14. The catheter of claim 13, wherein a third plurality of voids of the reinforcing layer located in said body portion are aligned in a circumferential direction of the balloon; the first plurality of voids being circumferentially aligned with the third plurality of voids.

15. The catheter of claim 10, wherein a plurality of said voids each comprise a serpentine band extending around a circumference of said balloon.

16. The catheter of claim 10, wherein the voids extend into the reinforcing layer from an outer surface of the balloon.

17. The catheter of claim 10, wherein the reinforcing layer comprises a perforated layer portion and an unperforated layer portion, the cavities extending through a full thickness of the perforated layer portion.

\* \* \* \* \*